(12) United States Patent
Muschaweck

(10) Patent No.: US 10,771,682 B2
(45) Date of Patent: Sep. 8, 2020

(54) CAMERA VIEWFINDER

(71) Applicant: Arnold & Richter Cine Technik GmbH & Co. Betriebs KG, Munich (DE)

(72) Inventor: Julius Muschaweck, Gauting (DE)

(73) Assignee: ARNOLD & RICHTER CINE TECHNIK GMBH & CO. BETRIEBS KG, Munich (DE)

( * ) Notice: Subject to any disclaimer, the term of this patent is extended or adjusted under 35 U.S.C. 154(b) by 42 days.

(21) Appl. No.: 15/485,912

(22) Filed: Apr. 12, 2017

(65) Prior Publication Data
US 2017/0302849 A1 Oct. 19, 2017

(30) Foreign Application Priority Data
Apr. 14, 2016 (DE) .......................... 10 2016 106 953

(51) Int. Cl.
*H04N 5/232* (2006.01)
*H04N 5/225* (2006.01)
(Continued)

(52) U.S. Cl.
CPC ....... *H04N 5/23219* (2013.01); *G02B 17/023* (2013.01); *G02B 23/14* (2013.01); *G02B 26/0825* (2013.01); *G02B 26/0875* (2013.01); *G02B 27/0068* (2013.01); *G03B 13/06* (2013.01); *G06K 9/0061* (2013.01); *G06K 9/00604* (2013.01); *G06K 9/00617* (2013.01); *H04N 5/2251* (2013.01);
(Continued)

(58) Field of Classification Search
None
See application file for complete search history.

(56) References Cited

U.S. PATENT DOCUMENTS 3,583,790 A 6/1971 Baker
4,812,864 A 3/1989 Baker
(Continued)

FOREIGN PATENT DOCUMENTS

DE   101 44 075 A1   4/2003
DE   10 2011 083 352 A1   3/2013
(Continued)

OTHER PUBLICATIONS

"Design of a freeform electronic viewfinder coupled to aberration fields of freeform optics"; Aaron Bauer and Jannick P. Rolland; published Oct. 19, 2015.
(Continued)

*Primary Examiner* — Frederick D Bailey
(74) *Attorney, Agent, or Firm* — Amster, Rothstein & Ebenstein LLP

(57) ABSTRACT

A camera viewfinder comprises an electronic display apparatus that is configured for the display of images that are recorded by an image sensor of an electronic camera. The camera viewfinder further comprises two mirrors for reflecting the images displayed by the display apparatus, of which at least one mirror is a free-form surface mirror whose reflective surface is formed as a free-form surface that does not have any continuous translation symmetry or rotational symmetry. At least one of the free-form surface mirrors is adjustable to at least partially compensate a vision defect of a user.

19 Claims, 2 Drawing Sheets

Figure 1:
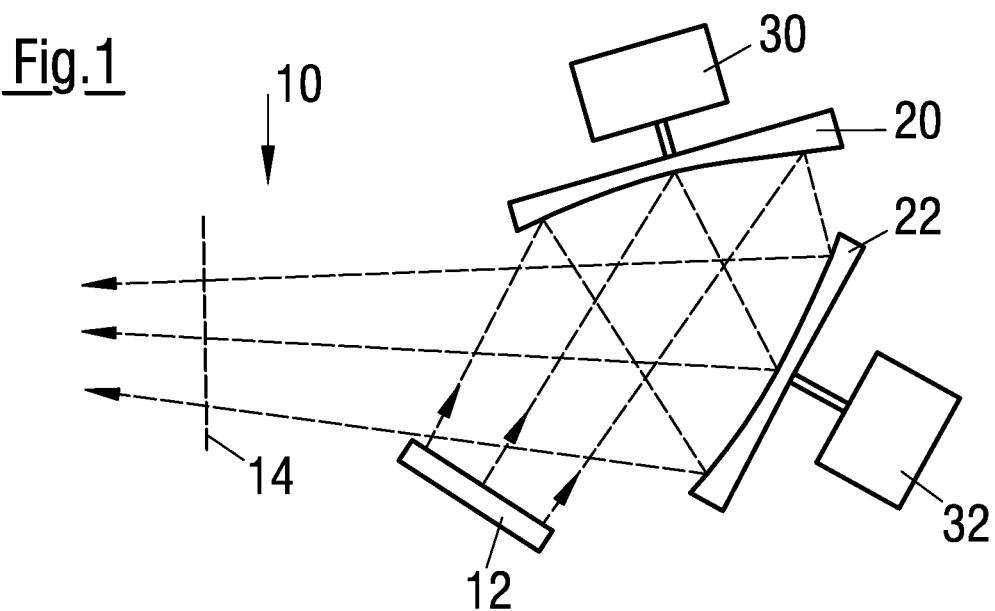

(51) Int. Cl.
*G06K 9/00* (2006.01)
*G03B 13/06* (2006.01)
*G02B 27/00* (2006.01)
*G02B 26/08* (2006.01)
*A61B 3/103* (2006.01)
*G02B 17/02* (2006.01)
*G02B 23/14* (2006.01)

(52) U.S. Cl.
CPC .......... *H04N 5/2256* (2013.01); *A61B 3/1035* (2013.01); *H04N 5/23293* (2013.01)

(56) References Cited

U.S. PATENT DOCUMENTS

| | | | | |
|---|---|---|---|---|
| 4,923,293 | A * | 5/1990 | Nelles | G02B 5/005 359/362 |
| 5,497,274 | A * | 3/1996 | Soll | A45D 42/24 132/316 |
| 5,903,788 | A | 5/1999 | Mukai et al. | |
| 6,166,859 | A | 12/2000 | Inuzuka et al. | |
| 6,259,564 | B1 * | 7/2001 | Kamo | G02B 17/0848 359/627 |
| 2003/0053027 | A1 | 3/2003 | Sarver | |
| 2003/0063400 | A1 | 4/2003 | Sunaga et al. | |
| 2003/0197943 | A1 | 10/2003 | Yamazaki et al. | |
| 2004/0090683 | A1 | 5/2004 | Nagata | |
| 2005/0088562 | A1 * | 4/2005 | Noto | H04N 5/2254 348/335 |
| 2006/0018045 | A1 * | 1/2006 | Moeller | G02B 5/10 359/838 |
| 2006/0209256 | A1 * | 9/2006 | Beyerlein | A61B 3/103 351/205 |
| 2008/0051933 | A1 * | 2/2008 | Vrachan | G02B 27/2292 700/231 |
| 2010/0045847 | A1 * | 2/2010 | Ryu | H04N 5/2253 348/341 |
| 2011/0019294 | A1 * | 1/2011 | Strong | G02B 7/04 359/823 |
| 2012/0038812 | A1 | 2/2012 | Neil | |
| 2016/0091723 | A1 | 3/2016 | Rolland et al. | |
| 2016/0262617 | A1 * | 9/2016 | Gerrans | A61B 3/18 |
| 2017/0115485 | A1 * | 4/2017 | Saito | B60K 35/00 |
| 2017/0227747 | A1 * | 8/2017 | Zhou | G02B 15/16 |

FOREIGN PATENT DOCUMENTS

| | | |
|---|---|---|
| EP | 0 689 075 A1 | 12/1995 |
| EP | 0 924 545 A1 | 6/1999 |
| EP | 1 97 767 A2 | 4/2002 |
| EP | 1 207 419 A2 | 5/2002 |
| EP | 1 251 691 A2 | 10/2002 |
| EP | 0 969 760 B1 | 10/2009 |
| JP | 2008-015475 | 2/2008 |

OTHER PUBLICATIONS

"Why are freeform telescopes less alignment sensitive than a traditional unobscured TMA?"; Kevin P. Thompson, Eric Schiesser, Jannick P. Rolland; Proc. SPIE 9633, Optifab 2015, 963317 (Oct. 11, 2015); doi:10.1117/12.2195784.

* cited by examiner

CAMERA VIEWFINDER

The present invention relates to a camera viewfinder having an electronic display apparatus that is configured for the display of images that are recorded by an image sensor of an electronic camera.

The respective image section recorded, i.e. converted into suitable electric signals, by the image sensor of the electronic camera can be viewed by means of the camera viewfinder. This image section can be displayed completely or partially by the electronic display apparatus and can be viewed by a user of the camera through a pre-assembled eyepiece, for example.

Such camera viewfinders can often only be used by users with vision defects with limitations, in particular when the user wears eyeglasses. If the camera viewfinder is used when eyeglasses are worn, the distance between the camera viewfinder and the eyes increases as a rule. Only a partial image area of the display apparatus is then frequently seen so that an ideal fixing of the image section to be recorded by the camera is no longer possible. If the camera viewfinder is, in contrast, used without eyeglasses, the vision defect of the user mostly remains uncorrected so that an evaluation of the image sharpness is only possible with restrictions if at all. A particularly common type of vision defect is astigmatism.

Camera viewfinders with an adjustable eyepiece are known that can compensate myopia or hyperopia of the user with certain limits, for example by a longitudinal displacement of the eyepiece lens. The weight, a large construction space due to the design, a complex correction of chromatic aberrations and high costs are disadvantageous in these camera viewfinders. A compensation of astigmatism is not provided.

It is therefore the object of the invention to provide an inexpensive, compact camera viewfinder that enables a vision defect of the user to be at least partially compensated.

The object is satisfied by a camera viewfinder having the features of claim 1.

The camera viewfinder in accordance with the invention comprises an electronic display apparatus that is configured for the display of images that are recorded by an image sensor of an associated electronic camera. The camera viewfinder further comprises at least two mirrors for reflecting the images displayed by the display apparatus. The respective image is in particular reflected by the at least two mirrors after one another along the optical light path, with the respective image being imaged—optionally via an additional lens arrangement—in the direction of the eye of a user. At least one of the mirrors is a free-form surface mirror whose reflective surface is designed as a free-form surface that does not have any continuous translation symmetry or rotational symmetry. At least one of the free-form surface mirrors, i.e. the only free-form surface mirror or at least one of a plurality of free-form surface mirrors of the camera viewfinder, is adjustable such that a vision defect of the user can be at least partially compensated by an adjustment of the respective free-form surface mirror.

The optical path of the camera viewfinder can be influenced in dependence on the design of the free-form surface using such free-form surface mirrors in a manner and in a compact form that is not possible with planar mirrors or with rotationally symmetrical mirrors (e.g. concave mirrors). Aberrations, also higher-order aberrations, can in particular be directly introduced into the optical path by a suitable selection of the free-form surface design that can compensate inherent aberrations of optical elements, including the eye of the user.

It has been recognized as part of the invention that the size of the aberration introduced by the free-form surface mirror is variable by an adjustment of such a freeform surface mirror, that is by a change of the position and/or of the alignment, to partially or completely compensate a vision defect of the user. An adjustable free-form surface mirror is thereby in particular suitable to compensate a vision defect of a user, in particular astigmatism. The adjustment of the free-form surface mirror or mirrors can take place both manually and by means of an actuator.

A free-form surface is to be understood in the context of the invention as a surface that does not have any continuous rotational symmetry or translation symmetry.

A continuous rotational symmetry is present when the surface can be generated by rotating a line (i.e. a curved path or a straight line) about an axis of rotation, wherein the rotation of the line takes place along a continuous angular range (i.e. by any desired angle within the angular range), and wherein the axis of rotation can be disposed within or outside the generated surface. For example, a hemispherical surface can be generated by a continuous rotation of a quadrant line by 360° with respect to a suitably aligned axis of rotation and a paraboloid can be generated by a continuous rotation of a parabola. Spherical lenses in which at least one refractive surface is formed by a section of a spherical surface and aspheric lenses in which at least one refractive surface can be formed by a continuous rotation of a curved path that is not an exact circular path have special significance in optics. The category of aspheric lenses in particular also comprises the embodiments in which the axis of rotation of the curved path is disposed outside the generated surface, i.e. in which the axis of rotation does not intersect the generated surface (so-called "off-axis aspheres"). The refractive surface of a spherical lens or of an aspheric lens therefore does not have any continuous rotational symmetry and can thus be produced in a simple manner (for example by rotation relative to a grinding tool); however, this is not yet a free-form surface in this respect. Corresponding deliberations naturally apply to the light-reflective surfaces of mirrors. A surface section of a torus can also be named as a further example for continuous rotational symmetry.

Continuous translation symmetry is present when the surface can be generated by translatory (i.e. straight-line) displacement of a line (i.e. of a curved path or of a straight line), with the displacement of the line taking place along a continuous path region (i.e. without interruptions). The generated surface of a half-cylinder can, for example, be generated by continuous translatory displacement of a semicircle, said generated surface having a continuous translation symmetry. So-called acylinders are produced by a continuous translation of a smooth curved path that is not a circular path; said acylinders deviate from generated cylinder surfaces in a comparable manner as aspheres from spheres. The parabolic trough mirrors in solar power plants are such acylinders, for example. Cylindrical lenses in which at least one refractive surface is formed by a section of a generated cylinder surface have special significance in optics. Acylindrical lenses are also used in classical imaging optics, for instance in anamorphic objectives. The refractive surface of a cylinder surface or of an acylinder therefore has a continuous translation symmetry and can be produced in a simple manner (for example, by a straight-line displacement of a milling tool relative to the lens). However, this is not yet a free-form surface in this respect.

In this context, "continuous symmetry" is to be understood as a difference from a discrete symmetry in which the generatrix is not displaced continuously, but rather at discrete intervals. A discrete rotational symmetry or translation symmetry of a surface does not preclude it being a free-form surface. For example, a free-form surface with respect to four quadrants can have a discrete rotational symmetry. Nor does a mirror symmetry of a surface preclude it being a free-form surface. A free-form surface can, for example, be mirror-symmetrical (left/right symmetry).

A free-form surface can thus have almost any desired form, whereby new possibilities arise for the configuration of the optical imaging properties. However, the conventional production methods for lenses and mirrors having continuous rotational symmetry or translation symmetry must be abandoned for this purpose.

The form of the free-form surface of the free-form surface mirror can be modeled, for example, by so-called Zernike polynomials that enable the desired imaging properties of the free-form surface to be mathematically defined.

The camera viewfinder can in particular only have mirrors that can at least also have an imaging function in addition to a deflecting function. It is, however, also possible to use a combination of mirrors and lenses. A variety of possibilities arise in the positioning and alignment of the mirrors with respect to one another, wherein, in comparison with a conventional camera viewfinder that only comprises lenses as optically active elements and therefore requires a purely linear arrangement of all the components, a reduction of the required construction space and thus a more compact arrangement can be achieved. The optical imaging path can be folded a multiple number of times by the use of mirrors, wherein in particular the plane of the display apparatus does not necessarily have to extend in parallel with the plane of the exit pupil such that the display apparatus can be arranged in a particularly space-saving manner. The camera viewfinder can in particular comprise three, four or five mirrors, with an improvement of the imaging performance tending to be achieved with a higher number of mirrors.

A further advantage of the use of mirrors, and in particular of free-form surface mirrors, instead of lenses, is the wavelength-independence of the imaging properties so that chromatic aberrations are avoided. The probability of the occurrence of ghost images such as can be the case with lenses due to an unwanted reflection at boundary surfaces is furthermore reduced. In addition, free-form surface mirrors can be produced inexpensively, and nevertheless with the required precision, for example by injection molding or by blank pressing.

In accordance with an advantageous embodiment, the at least one adjustable free-form surface mirror can be tiltable about at least one axis and/or can be movable in a translatory manner in at least one spatial direction. A translatory movement in only one spatial direction means that the respective free-form surface mirror is only moved in a straight line along this spatial direction. In the context of the invention, a tilting about an axis is considered as a possible degree of freedom of the adjustment of a free-form surface mirror; a tilting about another axis as a further possible degree of freedom; a translatory movement in a spatial direction as a further possible degree of freedom; and a translatory movement in another spatial direction as yet a further degree of freedom. Six degrees of freedom (three degrees of freedom of the tilt and three degrees of freedom of the translatory movability) are thus generally present with a completely freely tiltable free-form surface mirror movable in a translatory manner.

In accordance with an advantageous embodiment, the at least one adjustable free-form surface mirror can be adjustable by at least two different degrees of freedom. A versatile compensation of vision defects can hereby be achieved.

In accordance with a particularly simple embodiment, one or more free-form surface mirrors are provided, wherein only a single free-form surface mirror is, however, adjustable, and indeed about two degrees of freedom. A versatile vision defect compensability can hereby be realized with a relatively small construction effort.

In accordance with an alternative embodiment, the camera viewfinder has at least two adjustable free-form surface mirrors that are adjustable in different degrees of freedom. The actuation for adjustment in a plurality of different degrees of freedom can hereby be simplified. For example, the two free-form surface mirrors can be tiltable about axes standing orthogonal with respect to one another. Each of the two free-form surface mirrors is preferably only adjustable by one degree of freedom. The respective support and the required actuators can hereby be particularly easily implemented. It is, however, also possible that at least one of the two free-form surface mirrors is adjustable by two or more degrees of freedom.

In each of the cases in which an adjustability of one or more free-form surface mirrors by at least two degrees of freedom is present, the free-form surface mirror or mirrors is/are preferably adjustable independently of one another in the named degrees of freedom, i.e. an adjustment in one degree of freedom can take place without an adjustment in the other degree of freedom.

In accordance with a further advantageous embodiment of the invention, the free-form surface of the adjustable free-form surface mirror is configured such that an adjustment of this free-form surface mirror generates astigmatism as the only or substantially the only aberration. Such a free-form surface mirror can be used directly for the correction of astigmatism of the user in that the astigmatism generated by this free-form surface mirror is opposite to the astigmatism of the eye of the user such that both—at least partially—cancel each other out. Since astigmatism is generated as practically the only aberration in this embodiment, it is at least substantially avoided that an adjustment of this free-form surface mirror generates other aberrations such as spherical aberration, coma, distortion or curvature of field that have to be corrected in turn. The astigmatism generated by the named free-form surface mirror is preferably a so-called field-constant astigmatism, i.e. astigmatism that is at least substantially constant over the total image field of the camera viewfinder.

It has been found to be advantageous if the at least one adjustable free-form surface mirror is formed from plastic and has a reflective metal coating. Such a free-form surface mirror can be produced inexpensively with a high imaging quality.

The at least one adjustable free-form surface mirror is advantageously rigid, i.e. not deformable. It is thereby ensured that mechanical forces acting on the free-form surface mirror—in particular during the adjustment—do not change its imaging properties.

In accordance with yet a further advantageous embodiment of the invention a lens arrangement having a variable focal length is provided in the optical path of the camera viewfinder to correct a refraction vision defect of the user. A refractive vision error is understood as a vision error in which the refractive power of the eye differs from an ideal refractive power, which is also known as farsightedness or shortsightedness in everyday language. The lens arrangement can comprise one or more optical lenses and is in particular provided at the user-side end of the optical path, i.e. in the region of the exit pupil of the camera viewfinder. In this case, the compensation of the vision defect by an adjustment of the free-form surface mirror can be limited to an astigmatism that may be present.

For example, the lens arrangement can comprise a pair of mutually displaceable Alvarez lenses. Such Alvarez lens pairs are produced from a refractive material, wherein one surface is formed as a free-form surface, with the thickness z of the lens at a point x, y being able to be described, for example, by the equation $z=axy^2+(a/3)x^3+bx$. The two lens elements neutralize one another to form a zero power on an exact overlap. On a mutual displacement in the x direction, the refractive power varies, with positive optical powers resulting to the one side and negative optical powers to the other side.

Alternatively, the lens arrangement can comprise at least one lens with a variable radius of curvature. Such a lens can, for example, be a polymer lens whose contour can be varied by application of an electric current. The refractive power can thereby be set within milliseconds. An example for such a lens is commercially available under the designation "optotune EL-16-40-TC-VIS-20D". The refractive force can be changed within a range of +/−10 diopters; the aperture width amounts to 16 mm.

In accordance with yet a further advantageous embodiment, the camera viewfinder comprises at least one electrically controllable actuator that is configured to adjust the at least one adjustable free-form surface mirror, in particular to tilt it or to move it in a translatory motion.

In accordance with a particularly advantageous embodiment, the camera viewfinder further comprises a light source and a control and evaluation device that is configured to control or to activate the light source to produce a punctiform light spot on the retina of the eye of the user. The camera viewfinder in this embodiment furthermore comprises an optoelectronic receiver apparatus connected to the control and evaluation device for receiving light scattered back from the eye. The control and evaluation device is configured to determine the degree of a vision defect of the user on the basis of the received light. The named optoelectronic receiver apparatus can in particular be configured as a wavefront sensor and can comprise an image sensor having a lens matrix, wherein the lens matrix produces images of the light spot on the image sensor. The degree of the vision defect can be determined on the basis of deviations of the positions of the light spot images from ideal positions that result with an optical path free of aberrations or with an eye without a vision defect. An exemplary wavefront sensor is also called a Shack-Hartmann sensor or a Hartmann-Shack sensor.

It is, for example, possible that the named light source (for producing a punctiform light spot on the retina of the eye of the user) comprises a laser light source that generates a thin laser beam (e.g. a few tenths of a mm) that is of low power and safe for the eyes.

The electronic display apparatus can advantageously, however, have a two-dimensional matrix of light-emitting display elements, wherein the light source (for generating a punctiform light sport on the retina of the eye of the user) comprises at least one display element of the display apparatus. For example, the display apparatus can be a so-called OLED ("organic light emitting diode") display whose display elements comprise light emitting diodes manufactured from an organic material. The control and evaluation device accordingly controls the display apparatus such that one or more adjacent display elements are directly activated. A separate light source (e.g. a laser light source) in the viewfinder can thereby be dispensed with.

In accordance with a further particularly advantageous embodiment, the camera viewfinder has at least one electrically controllable actuator (in particular the already named actuator) that is configured to adjust the at least one adjustable free-form surface mirror, and wherein the control and evaluation device is configured to transmit a control command to the actuator on the basis of the determined degree of the vision defect of the user to adjust the at least one adjustable free-form surface mirror such that the determined vision defect is at least partially compensated. The vision defect of the user can thereby be automatically corrected without any further treatments of the user. A user input is at most required to initiate the measurement and correction of the measured vision defect.

The camera viewfinder can advantageously have a storage device that is connected to the control and evaluation device and that is configured to store user-specific data records that represent the degree of the vision defect of a respective user and/or that represent control commands to the actuator required to compensate the vision defect of a respective user. The control and evaluation device can be configured in this embodiment to control the actuator on the basis of a data record transmitted by the storage device. The camera viewfinder can thereby be adapted to different vision defects with changing users without the above-described measurement procedure having to be carried out on every change of user. The camera viewfinder can comprise an operating device for storing and/or invoking a desired user-specific data record.

A field lens can advantageously be arranged on the display apparatus to correct a curvature of field and/or telecentricity errors as required.

The present invention further relates to an electronic camera having a camera viewfinder in accordance with one of the above-described embodiments that is in accordance with the invention and/or advantageous. Such an electronic camera furthermore comprises an electronic image sensor and an associated electronic reader circuit. The signals generated independently of the exposure by the image sensor can be read by means of the reader circuit and can be forwarded to a storage device of the camera or to an output interface. The signals generated by the image sensor can be supplied to the electronic display apparatus of the camera viewfinder, in particular via the reader circuit. Such an electronic camera is known from US 2015/0070559 A1, for example.

Further advantageous embodiments of the invention result from the dependent claims, from the description and from the drawings.

Figure 2:
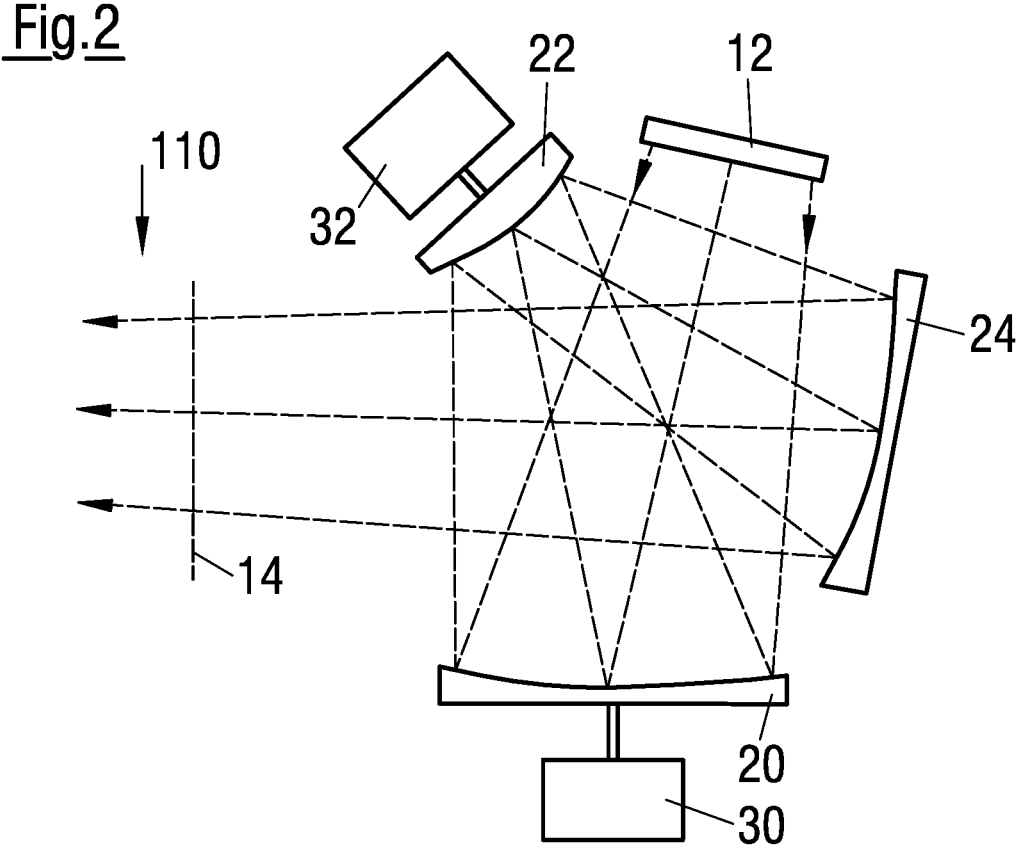
Figure 3:
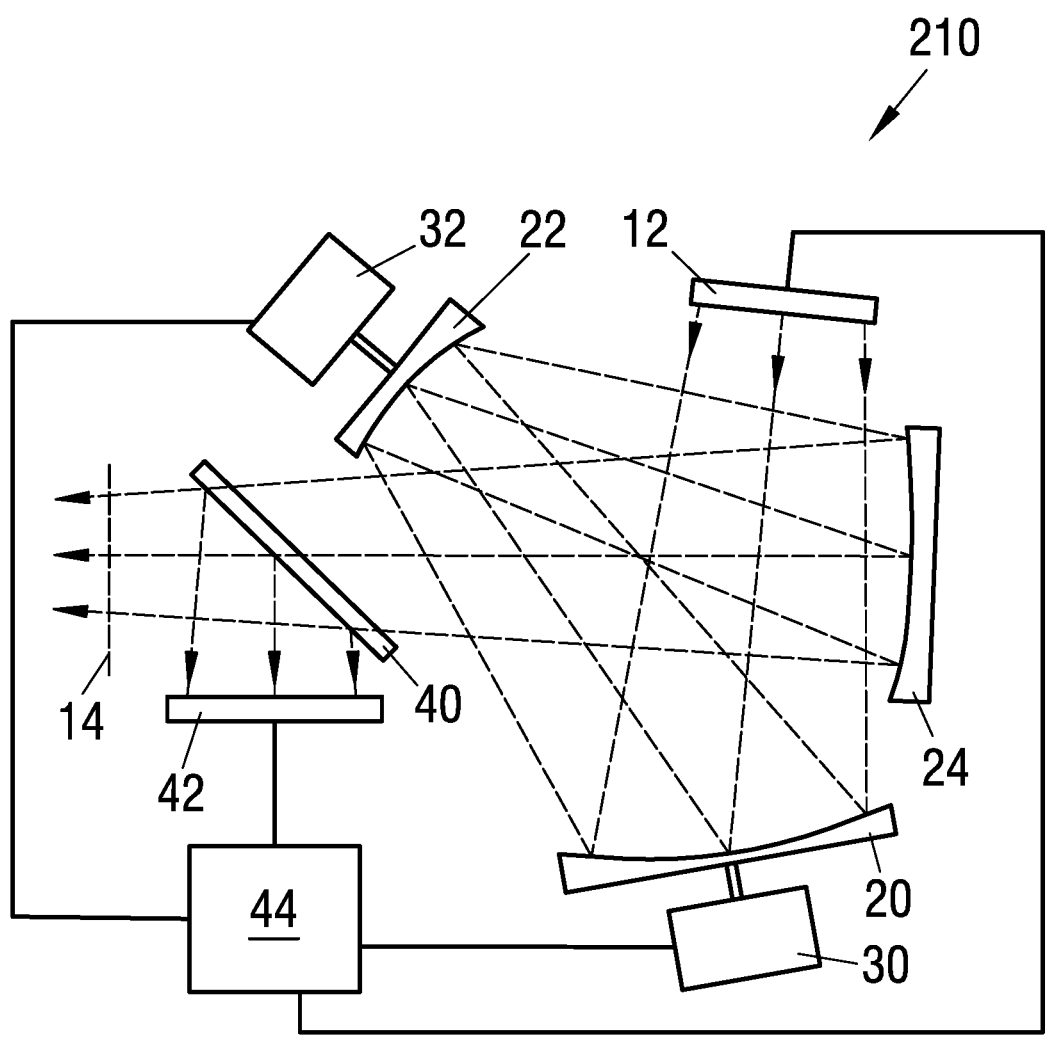

The invention will be described in the following with reference to embodiments and to the drawings. There are shown:

FIG. 1 a schematic representation of a camera viewfinder in accordance with the invention in accordance with a first embodiment;

FIG. 2 a schematic representation of a camera viewfinder in accordance with the invention in accordance with a second embodiment; and FIG. 3 a schematic representation of a camera viewfinder in accordance with the invention in accordance with a third embodiment.

FIG. 1 shows a camera viewfinder 10 in accordance with the invention in accordance with a first embodiment. The camera viewfinder 10 comprises an electronic display apparatus 12 having a two-dimensional matrix of display elements, for example a so-called OLED display. The light irradiated by the display apparatus 12, that is the image displayed by the display apparatus 12, is first incident onto a first mirror 20 and is deflected by it in the direction of a second mirror 22. The light deflected by the second mirror 22 passes through an exit pupil 14 from the camera viewfinder 10 and can there pass into the eye of a user (not shown). Both mirrors 20, 22 have imaging properties, wherein one of the mirrors, preferably both mirrors 20, 22 are preferably configured as free-form surface mirrors. The reflective surface of the mirrors 20, 22 can be described, for example, by Zernike polynomials.

Each mirror 20, 22 is coupled to an actuator 30 and 32 respectively. The first mirror 20 can be tilted about a first axis with the aid of the actuator 30 and the second mirror 22 can be tilted about a second axis by means of the actuator 32, wherein the two axes preferably extend orthogonally with respect to one another. Manual adjustment apparatus can also be provided instead of the actuators 30, 32.

The astigmatism changes in a direction predefined by the respective tilt axis by a tilt of the mirrors 20, 22. A degree of astigmatism that is suitable to compensate an astigmatism present in the eye of the user completely or at least to a large extent can be added to the optical path of the camera viewfinder 10 by a suitable selection of the respective tilt angles.

FIG. 2 shows a camera viewfinder 110 in accordance with a second embodiment. The camera viewfinder 110 substantially corresponds to features of the camera viewfinder 10 (FIG. 1) so that the same elements or similar elements are provided with the same reference numerals. In addition to a first and second mirror 20, 22, a third mirror 24 is provided that likewise has imaging properties and can in particular be configured as a free-form surface mirror. The third mirror 24 is provided in the optical path between the second mirror 22 and the exit pupil 14.

In accordance with a modification, further mirrors, for example a total of four or five mirrors, can also be provided. All of these mirrors do not necessarily have to be configured as free-form surface mirrors; for example, spherical or planar mirrors can also be used for the beam shaping and/or beam deflection to ensure an ideal imaging quality and/or to achieve a construction shape of the camera viewfinder that is as compact as possible.

In accordance with a further modification, actuators 30, 32 can also be used that effect a change of the astigmatism by means of a displacement of the respective mirror 20, 22 on a use of a suitable free-form surface Such a displacement of one or more mirrors 20, 22 can in particular also be used to effect a focusing or defocusing.

In accordance with yet a further modification, instead of two mirrors 20, 22 that are each adjustable in one degree of freedom, a single mirror configured as a free-form surface mirror can be connected to an actuator that can adjust this mirror using two degrees of freedom. For example, these two degrees of freedom can correspond to a tilt of the mirror about two mutually orthogonal axes.

It must be noted for reasons of completeness that the arrangements of the two mirrors 20, 22 (FIG. 1) or of the three mirrors 20, 22, 24 (FIG. 2) are purely by way of example. In particular the angles and distances between the display apparatus 12, the mirrors 20, 22, 24 and the exit pupil 14 as well as the imaging properties of the mirrors 20, 22, 24 can thus be varied as desired. The sequence of adjustable and fixed-position mirrors and of conventional mirrors and free-form surface mirrors within the arrangement can also vary in the embodiments shown and in further modifications. Unwanted aberrations such as distortion or coma can be minimized and unwanted scattered light can be avoided by a selection of a suitable configuration.

A camera viewfinder 210 in accordance with a third embodiment shown in FIG. 3 substantially corresponds to the camera viewfinder 110 of FIG. 2. The camera viewfinder 210 additionally comprises a control and evaluation device 44 that is connected to the display apparatus 12, to the actuators 30, 32, and to an optoelectronic receiver apparatus 42 to communicate therewith and in particular to transmit control commands.

The receiver apparatus 42 is configured or determining aberrations and is in particular used to determine a vision defect of the user. The receiver apparatus 42 can, for example, be configured as a wavefront sensor, in particular as a so-called Shack-Hartmann sensor, and can comprise an image sensor having a lens matrix connected in front of it, wherein the lens matrix produces images of the light spot on the image sensor. Existing aberrations can be determined on the basis of deviations of the positions of the light spot images from ideal positions that apply to an optical path without aberrations.

The control and evaluation device 44 can control the display apparatus 12 such that one or more mutually adjacent display elements of the display apparatus 12 are activated, while the display elements arranged in the vicinity for this purpose at least remain substantially dark such that the activated display element(s) form(s) a point light source. A punctiform light sport can hereby be produced on the retina of the eye of a user looking into the camera viewfinder 210—without the necessity of a separate light source. Light scattered back from the eye is directed to the receiver apparatus 42 by means of a partially transmitting mirror 40 that is arranged between the exit pupil 14 and the third mirror 24 and that can be located in the optical path temporarily for the carrying out of the determination of the vision defect or permanently. The control and evaluation device 44 is configured to determine the degree of a vision defect of the user, in particular astigmatism, on the basis of the received light and in particular on the basis of the detected form of the wavefront scattered back.

The control and evaluation device 44 generates corresponding control commands for the actuators 30, 32 on the basis of the determined degree of the vision defect, said control commands having the effect that the determined vision defect is at least largely compensated by a corresponding adjustment of the mirrors 20, 22, coupled to the actuators 30, 32. The degree of the vision defect determined for a user or the corresponding control commands for the actuators 30, 32 can optionally be stored in a non-volatile memory of the control and evaluation device 44 (not shown) and are hereby available fast for a later invocation.

REFERENCE NUMERAL LIST 10, 110, 210 camera viewfinder 12 display apparatus 14 exit pupil 20, 22, 24 mirror 30, 32 actuator 40 partially transmitting mirror 42 receiver apparatus 44 control and evaluation device

The invention claimed is:

1. A camera viewfinder (10) of an electronic camera, comprising
an electronic display apparatus (12) that is configured for the display of images that are recorded by an image sensor of the electronic camera; and
at least two mirrors (20, 22, 24) for reflecting the images displayed by the display apparatus (12), of which at least one mirror is a free-form surface mirror (20, 22, 24) whose reflective surface is formed as a free-form surface that has no continuous translation symmetry or rotational symmetry and which is not deformable,
wherein at least one of the free-form surface mirrors (20, 22, 24) is adjustable during use of the electronic camera to at least partially compensate a vision defect of a user,
wherein the at least one free-form surface mirror (20, 22, 24) is adjustable during use of the electronic camera in accordance with at least one of the following:
a) the at least one adjustable free-form surface mirror (20, 22, 24) can be tilted about at least one axis; and
b) the at least one adjustable free-form surface mirror (20, 22, 24) is movable in a translatory manner in at least one spatial direction so that the at least one free-form surface mirror is movable in a straight line along the at least one spatial direction.

2. A camera viewfinder (10) in accordance with claim 1, wherein the at least one adjustable free-form surface mirror (20, 22, 24) is configured to at least partially compensate a field-constant astigmatism of the user by the tilting about the at least one axis.

3. A camera viewfinder (10) in accordance with claim 1, wherein the at least one adjustable free-form surface mirror (20, 22, 24) is tiltable about at least one axis and is movable in a translatory manner in at least one spatial direction.

4. A camera viewfinder (10) in accordance with claim 1, wherein the at least one adjustable free-form surface mirror (20, 22, 24) is adjustable by at least two different degrees of freedom.

5. A camera viewfinder (10) in accordance with claim 1, wherein the camera viewfinder (10) has at least two adjustable free-form surface mirrors that are adjustable in different degrees of freedom.

6. A camera viewfinder (10) in accordance with claim 1, wherein the free-form surface of the adjustable free-form surface mirror (20, 22, 24) is configured such that an adjustment of this free-form surface mirror (20, 22, 24) generates an astigmatism as at least substantially the only aberration.

7. A camera viewfinder (10) in accordance with claim 1, wherein the at least one adjustable free-form surface mirror (20, 22, 24) is formed from plastic and has a reflective metal coating.

8. A camera viewfinder (10) in accordance with claim 1, wherein a lens arrangement with variable focal length is provided in the optical path of the camera viewfinder (10) for the correction of a refractive vision defect of the user.

9. A camera viewfinder (10) in accordance with claim 8, wherein the lens arrangement comprises a pair of mutually displaceable Alvarez lenses.

10. A camera viewfinder (10) in accordance with claim 8, wherein the lens arrangement comprises at least one lens having a variable radius of curvature.

11. A camera viewfinder (10) in accordance with claim 1, furthermore comprising at least one electrically controllable actuator (30, 32) that is configured to adjust the at least one adjustable free-form surface mirror (20, 22, 24).

12. A camera viewfinder (10) in accordance with claim 1, furthermore comprising a light source; a control and evaluation device (44) that is configured to activate the light source to generate a punctiform light spot on the retina of the eye of the user; and an optoelectronic receiver apparatus (42) connected to the control and evaluation device (44) for receiving light scattered back from the eye, with the control and evaluation device (44) being configured to determine a degree of a vision defect of the user on the basis of the received light.

13. A camera viewfinder (10) in accordance with claim 12, wherein the electronic display apparatus (12) has a two-dimensional matrix of light-emitting display elements; and wherein the light source comprises at least one display element of the display apparatus (12).

14. A camera viewfinder (10) in accordance with claim 12, wherein the camera viewfinder (10) has at least one electrically controllable actuator (30, 32) that is configured to adjust the at least one adjustable free-form surface mirror (20, 22, 24); and wherein the control and evaluation device (44) is configured to transmit a control command to the actuator (30, 32) on the basis of the determined degree of the vision defect of the user to adjust the at least one adjustable free-form surface mirror (20, 22, 24) such that the determined vision defect is at least partially adjusted.

15. A camera viewfinder (10) in accordance with claim 14, wherein the camera viewfinder (10) has a storage device that is connected to the control and evaluation device (44) and that is configured to store user-specific data records, with the control and evaluation device (44) being configured to control the actuator (30, 32) on the basis of a data record transmitted by the storage device, and with the user-specific data records representing at least one of the following: the degree of the vision defect of a respective user, or control commands to the actuator (30, 32) required to compensate the vision defect of a respective user.

16. An electronic camera comprising a camera viewfinder (10) in accordance with claim 1.

17. A camera viewfinder comprising at least:
an electronic display configured for displaying an image;
a first mirror that reflects the image displayed by the electronic display, and
a second mirror that reflects the image displayed by the electronic display and reflected by the first mirror,
wherein at least one of the first mirror and second mirror is a free-form surface mirror that has a reflective surface formed as a free-form surface that has no continuous translation symmetry or rotational symmetry and which is not deformable,
wherein at least one of a position and an orientation of the free-form surface mirror is adjustable during use of the camera viewfinder,
wherein the free-form surface mirror is adjustable during use of the camera viewfinder in accordance with at least one of the following:
a) the free-form surface mirror can be tilted about at least one axis; and b) the free-form surface mirror is movable in a translatory manner in at least one spatial direction so that the at least one free-form surface mirror is movable in a straight line along the at least one spatial direction.

18. A camera viewfinder of an electronic camera, comprising an electronic display apparatus that is configured for the display of images that are recorded by an image sensor of the electronic camera; and at least two mirrors for reflecting the images displayed by the display apparatus, of which at least one mirror is a free-form surface mirror whose reflective surface is formed as a free-form surface that has no continuous translation symmetry or rotational symmetry, wherein at least one of the free-form surface mirrors is adjustable during use of the electronic camera to at least partially compensate a vision defect of a user, and wherein the at least one of the free-form surface mirrors is not deformable.

19. A camera viewfinder (10) of an electronic camera, comprising an electronic display apparatus (12) that is configured for the display of images that are recorded by an image sensor of the electronic camera; and at least two mirrors (20, 22, 24) for reflecting the images displayed by the display apparatus (12), of which at least one mirror is a free-form surface mirror (20, 22, 24) whose reflective surface is formed as a free-form surface that has no continuous translation symmetry or rotational symmetry and which is not deformable, wherein at least one of the free-form surface mirrors (20, 22, 24) is adjustable during use of the electronic camera to at least partially compensate a vision defect of a user, wherein the at least one free-form surface mirror (20, 22, 24) is adjustable during use of the electronic camera in accordance with at least one of the following:

a) the at least one adjustable free-form surface mirror (20, 22, 24) can be tilted about at least one axis; and b) the at least one adjustable free-form surface mirror (20, 22, 24) is movable in a translatory manner in at least one spatial direction so that the at least one free-form surface mirror is movable in a straight line along the at least one spatial direction, the camera viewfinder further comprising:

a light source;

a control and evaluation device that is configured to activate the light source to generate a punctiform light spot on the retina of the eye of the user;

an optoelectronic receiver apparatus connected to the control and evaluation device for receiving light scattered back from the eye, with the control and evaluation device being configured to determine a degree of a vision defect of the user on the basis of the received light; and at least one electrically controllable actuator that is configured to adjust the at least one adjustable free-form surface mirror, wherein the control and evaluation device is configured to transmit a control command to the actuator on the basis of the determined degree of the vision defect of the user to adjust the at least one adjustable free-form surface mirror such that the determined vision defect is at least partially adjusted.

* * * * *